US012702510B2

(12) United States Patent
Brisson et al.

(10) Patent No.: US 12,702,510 B2
(45) **Date of Patent: *Aug. 11, 2026**

(54) CONTROL INPUT ACCURACY FOR TELEOPERATED SURGICAL INSTRUMENT

(71) Applicant: INTUITIVE SURGICAL OPERATIONS, INC., Sunnyvale, CA (US)

(72) Inventors: Gabriel F. Brisson, Sunnyvale, CA (US); Niels Smaby, Palo Alto, CA (US); Melody Wu, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 657 days.

This patent is subject to a terminal disclaimer.

(21) Appl. No.: 18/171,246

(22) Filed: Feb. 17, 2023

(65) Prior Publication Data

US 2023/0277264 A1 Sep. 7, 2023

Related U.S. Application Data

(63) Continuation of application No. 16/131,925, filed on Sep. 14, 2018, now Pat. No. 11,607,282, which is a (Continued)

(51) Int. Cl.
*A61B 34/35* (2016.01)
*A61B 17/00* (2006.01)
(Continued)

(52) U.S. Cl.
CPC .............. *A61B 34/37* (2016.02); *A61B 17/00* (2013.01); *A61B 34/35* (2016.02); *F16D 63/006* (2013.01);
(Continued)

(58) Field of Classification Search
CPC ......... A61B 34/37; A61B 17/00; A61B 34/35; A61B 17/07207; A61B 2017/00398;
(Continued)

(56) References Cited

U.S. PATENT DOCUMENTS 5,184,601 A 2/1993 Putman
5,445,166 A 8/1995 Taylor et al.
(Continued)

FOREIGN PATENT DOCUMENTS

CN 101791233 A 8/2010
CN 103584918 A 2/2014
(Continued)

OTHER PUBLICATIONS

Extended European Search Report for Application No. EP15773874.1, mailed on Nov. 7, 2017, 7 pages.
(Continued)

*Primary Examiner* — Benjamin J Klein
*Assistant Examiner* — Alisha J Sircar
(74) *Attorney, Agent, or Firm* — Haynes & Boone, LLP.

(57) ABSTRACT

A method comprises driving, by a motor, a camshaft of a transmission of a telesurgically operated instrument to a first rotational state of a plurality of rotational states. The camshaft defines a longitudinal axis and rotates about the longitudinal axis. The method further comprises engaging, in the first rotational state, a first input gear of a first effector drivetrain of the transmission with a first gear of the first effector drivetrain via a first power cam of the camshaft. The method further comprises disengaging, in the first rotational state, a first locker arm of the first effector drivetrain from the first gear via a first locker cam of the camshaft.

20 Claims, 11 Drawing Sheets

Related U.S. Application Data continuation of application No. 15/128,234, filed as application No. PCT/US2015/023629 on Mar. 31, 2015, now Pat. No. 10,098,705.

(60) Provisional application No. 61/973,822, filed on Apr. 1, 2014.

(51) Int. Cl.

| | |
|---|---|
| ***A61B 34/37*** | (2016.01) |
| ***F16D 63/00*** | (2006.01) |
| *A61B 17/072* | (2006.01) |
| *A61B 90/00* | (2016.01) |

(52) U.S. Cl.

CPC ............... *A61B 2017/00398* (2013.01); *A61B 17/07207* (2013.01); *A61B 2090/031* (2016.02)

(58) Field of Classification Search

CPC ... A61B 2090/031; A61B 34/70; A61B 50/13; F16D 63/006

See application file for complete search history.

(56) References Cited

U.S. PATENT DOCUMENTS

| | | | | |
|---|---|---|---|---|
| 5,800,423 | A | 9/1998 | Jensen et al. | |
| 5,807,378 | A | 9/1998 | Jensen et al. | |
| 5,808,665 | A | 9/1998 | Green et al. | |
| 5,855,583 | A | 1/1999 | Wang et al. | |
| 6,246,200 | B1 | 6/2001 | Blumenkranz et al. | |
| 6,676,669 | B2 | 1/2004 | Charles et al. | |
| 6,702,805 | B1 | 3/2004 | Stuart et al. | |
| 6,758,843 | B2 | 7/2004 | Jensen et al. | |
| 6,788,018 | B1 | 9/2004 | Blumenkranz | |
| 7,594,912 | B2 | 9/2009 | Cooper et al. | |
| 7,763,015 | B2 | 7/2010 | Cooper et al. | |
| 8,616,431 | B2 | 12/2013 | Timm et al. | |
| 8,870,912 | B2 | 10/2014 | Brisson et al. | |
| 8,876,857 | B2 | 11/2014 | Burbank | |
| 9,730,719 | B2 | 8/2017 | Brisson et al. | |
| 10,098,705 | B2 | 10/2018 | Brisson et al. | |
| 11,607,282 | B2 * | 3/2023 | Brisson .................. | A61B 34/37 |
| 2006/0100610 | A1 | 5/2006 | Wallace et al. | |
| 2006/0261770 | A1 | 11/2006 | Kishi et al. | |
| 2008/0058776 | A1 | 3/2008 | Jo et al. | |
| 2009/0101692 | A1 | 4/2009 | Whitman et al. | |
| 2011/0040308 | A1 * | 2/2011 | Cabrera ............. | A61B 17/0491<br>606/144 |
| 2011/0118709 | A1 | 5/2011 | Burbank | |
| 2011/0180985 | A1 | 7/2011 | Yamamoto | |
| 2012/0199632 | A1 | 8/2012 | Spivey et al. | |
| 2012/0310254 | A1 | 12/2012 | Manzo et al. | |
| 2013/0325034 | A1 | 12/2013 | Schena et al. | |
| 2014/0000411 | A1 * | 1/2014 | Shelton, IV ........... | A61B 34/37<br>74/650 |
| 2014/0001234 | A1 | 1/2014 | Shelton, IV et al. | |
| 2017/0172672 | A1 | 6/2017 | Bailey et al. | |
| 2019/0083188 | A1 | 3/2019 | Brisson et al. | |

FOREIGN PATENT DOCUMENTS

| | | | |
|---|---|---|---|
| EP | 0890344 | A2 | 1/1999 |
| EP | 3187124 | A1 | 7/2017 |
| JP | S62292945 | A | 12/1987 |
| JP | 2012061195 | A | 3/2012 |
| WO | WO-2011060318 | A1 | 5/2011 |
| WO | WO-2011143016 | A1 | 11/2011 |
| WO | WO-2011143338 | A1 | 11/2011 |
| WO | WO-2012068156 | A2 | 5/2012 |
| WO | WO-2012166807 | A1 | 12/2012 |
| WO | WO-2015153636 | A1 | 10/2015 |

OTHER PUBLICATIONS

Extended European Search Report for Application No. EP19150570, mailed on May 3, 2019, 8 pages.

International Search Report and Written Opinion for Application No. PCT/US15/23629, mailed on Jun. 10, 2015, 11 pages.

Vertut, J, and Coiffet, P., "Robot Technology: Teleoperation and Robotics Evolution and Development," English translation, Prentice Hall, Inc., Inglewood Cliffs, NJ, USA 1986, vol. 3A, 332 pages.

* cited by examiner

CONTROL INPUT ACCURACY FOR TELEOPERATED SURGICAL INSTRUMENT

CROSS-REFERENCE TO RELATED APPLICATIONS

This application is a continuation of U.S. patent application Ser. No. 16/131,925, filed Sep. 14, 2018, which is a continuation of U.S. patent application Ser. No. 15/128,234, now U.S. Pat. No. 10,098,705, filed Sep. 22, 2016, which is the U.S. national phase of International Application No. PCT/US2015/023629, filed Mar. 31, 2015, which designated the U.S. and which is related to and claims priority to and the benefit of U.S. Provisional Application No. 61/973,822 filed Apr. 1, 2014, entitled "CONTROL INPUT ACCURACY FOR TELEOPERATED SURGICAL INSTRUMENT" by Brisson, et al. The contents of each of the above listed applications are incorporated herein by reference in their entirety and for all purposes.

BACKGROUND OF THE INVENTION

Minimally invasive medical techniques are intended to reduce the amount of extraneous tissue that is damaged during diagnostic or surgical procedures, thereby reducing patient recovery time, discomfort, and deleterious side effects. One effect of minimally invasive surgery, for example, is reduced post-operative hospital recovery times. Because the average hospital stay for a standard surgery is typically significantly longer than the average stay for an analogous minimally invasive surgery, increased use of minimally invasive techniques could save millions of dollars in hospital costs each year. While many of the surgeries performed each year in the United States could potentially be performed in a minimally invasive manner, only a portion of the current surgeries use these advantageous techniques due to limitations in minimally invasive surgical instruments and the additional surgical training involved in mastering them.

Minimally invasive telesurgical systems have been developed to increase a surgeon's dexterity and avoid some of the limitations on traditional minimally invasive techniques. In telesurgery, the surgeon uses some form of remote control (e.g., a servomechanism or the like) to manipulate surgical instrument movements, rather than directly holding and moving the instruments by hand. In telesurgery systems, the surgeon can be provided with an image of the surgical site at a surgical workstation. While viewing a two or three dimensional image of the surgical site on a display, the surgeon performs the surgical procedures on the patient by manipulating master control devices, which in turn control motion of the servo-mechanically operated instruments.

The servomechanism used for telesurgery will often accept input from two master controllers (one for each of the surgeon's hands) and may include two or more robotic arms on each of which a surgical instrument is mounted. Operative communication between master controllers and associated robotic arm and instrument assemblies is typically achieved through a control system. The control system typically includes at least one processor that relays input commands from the master controllers to the associated robotic arm and instrument assemblies and back from the instrument and arm assemblies to the associated master controllers in the case of, for example, force feedback or the like. One example of a robotic surgical system is the DA VINCI® system available from Intuitive Surgical, Inc. of Sunnyvale, California, USA.

A variety of structural arrangements can be used to support the surgical instrument at the surgical site during robotic surgery. The driven linkage or "slave" is often called a robotic surgical manipulator, and exemplary linkage arrangements for use as a robotic surgical manipulator during minimally invasive robotic surgery are described in U.S. Pat. Nos. 7,594,912; 6,758,843; 6,246,200; and 5,800,423; which are incorporated herein by reference. These linkages often make use of a parallelogram arrangement to hold an instrument having a shaft. Such a manipulator structure can constrain movement of the instrument so that the instrument pivots about a remote center of manipulation positioned in space along the length of the rigid shaft. By aligning the remote center of manipulation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing potentially dangerous forces against the abdominal wall. Alternative manipulator structures are described, for example, in U.S. Pat. Nos. 7,763,015; 6,702,805; 6,676,669; 5,855,583; 5,808,665; 5,445,166; and 5,184,601; which are incorporated herein by reference.

A variety of structural arrangements can also be used to support and position the robotic surgical manipulator and the surgical instrument at the surgical site during robotic surgery. Supporting linkage mechanisms, sometimes referred to as set-up joints, or set-up joint arms, are often used to position and align each manipulator with the respective incision point in a patient's body. The supporting linkage mechanism facilitates the alignment of a surgical manipulator with a desired surgical incision point and targeted anatomy. Exemplary supporting linkage mechanisms are described in U.S. Pat. Nos. 6,246,200 and 6,788,018, which are incorporated herein by reference.

While the new telesurgical systems and devices have proven highly effective and advantageous, still further improvements are desirable. In general, improved minimally invasive robotic surgery systems are desirable. Often, new surgical instruments are developed for use on existing telesurgical system platforms. Thus, the instrument is required to adapt to the telesurgical system, since development of a new telesurgical system for a particular surgical application is cost prohibitive. However, issues arise when existing telesurgical platforms do not have the required amount of motor outputs for all of the mechanisms of a particular surgical instrument. Thus, there is a need to adapt new surgical devices to existing telesurgical systems without limiting the surgical capabilities and without requiring modification to the existing telesurgical systems.

BRIEF SUMMARY OF THE INVENTION

Many embodiments are directed to a surgical tool comprising an elongated shaft having a proximal end and distal end. A surgical effector is located about the distal end. The surgical effector may include a plurality of effector mechanisms, each effector mechanism having one or a plurality of degree of freedoms (DOFs). An effector body may also be located at the proximal end. The effector body may include a plurality of motor interfaces for driving the plurality of effector mechanisms. For example, the plurality of motor interfaces may include a first motor interface. A transmission may be coupled between the effector body and the surgical effector. The transmission may be configured to shift coupling of the first motor interface between only a portion of the plurality of effector mechanisms and associated DOFs.

Many embodiments are directed a surgical system having a patient side cart having at least one telesurgically operated instrument. The at least one telesurgically operated instrument includes a surgical effector having a plurality of effector mechanisms. A transmission is provided for coupling the plurality of effector mechanisms to a motor. The drive train includes at least a first effector drive train and a second effector drivetrain. A controller is provided and includes at least one processor for controlling the transmission. The controller is configured to perform a method by locking an output gear of the second effector drivetrain. A camshaft is then rotated to shift coupling of the motor from the first effector drivetrain to the second effector drivetrain. It is determined that the output gear is aligned by driving the locked output gear using a first torque. It is then determined that the output gear is properly braked by driving the locked output gear using a second torque. The output gear can then be unlocked and the second effector drivetrain can be driven using the motor.

In many embodiments, the first torque is relatively lower than the second torque.

In many embodiments, determining that the output gear is aligned comprises determining whether movement of the output gear stalls under the first torque.

In many embodiments, if movement of the output gear stalls under the first torque then the output gear is determined to be aligned.

In many embodiments, if movement of the output gear does not stall under the first torque then the output gear is determined to be misaligned and shifting the transmission aborted.

In many embodiments, determining that the output gear is properly braked comprises determining whether the second torque applied by the motor is a saturated value.

In many embodiments, if the second torque reaches the saturated value then the output gear is properly braked.

In many embodiments, if the relatively high torque does not reach the saturated value then the output gear is not properly braked and shifting the transmission is aborted.

DETAILED DESCRIPTION OF THE INVENTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

I. Minimally Invasive Teleassisted Surgery System

Figure 1:
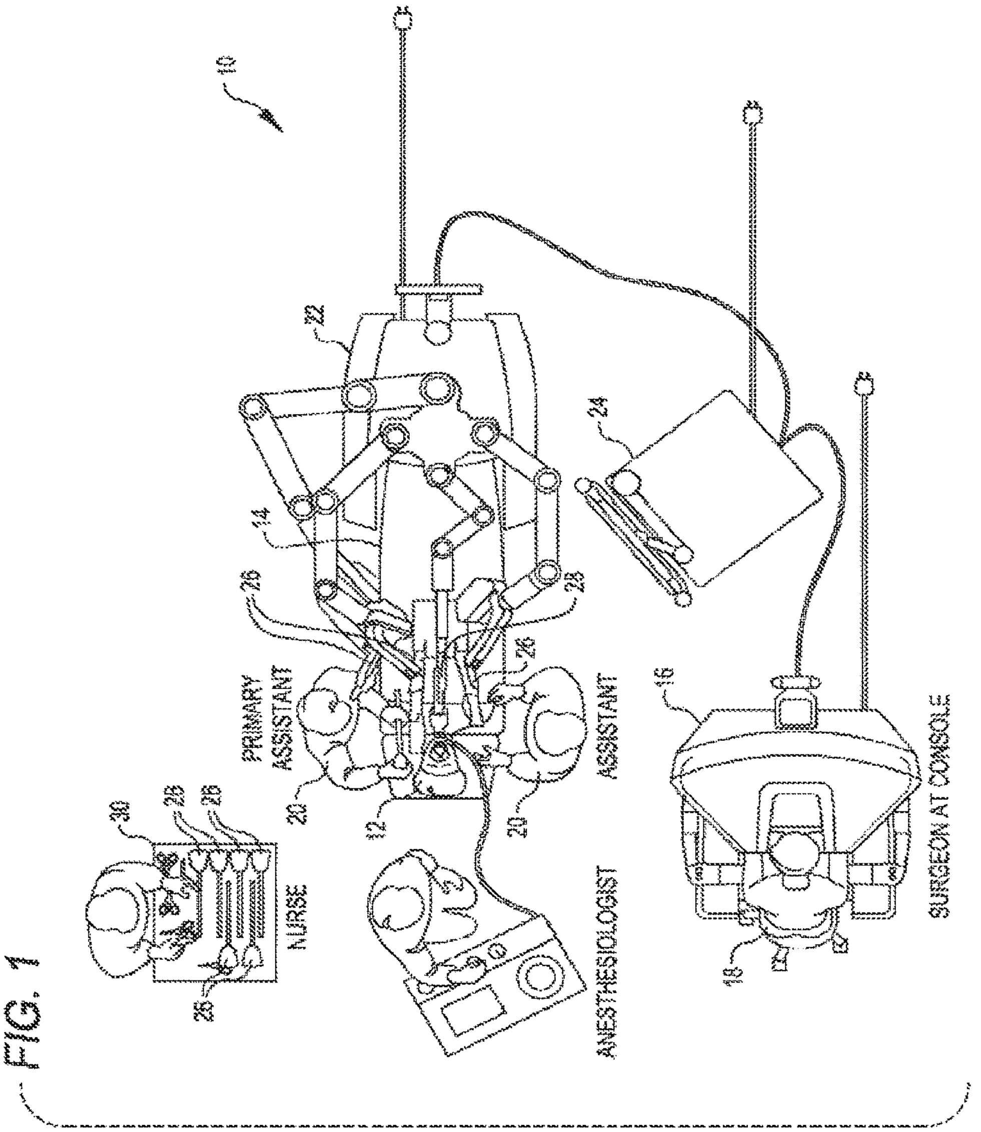
FIG. 1 is a plan view of a minimally invasive telesurgically controlled surgery system being used to perform a surgery, in accordance with many embodiments.

Referring now to the drawings, in which like reference numerals represent like parts throughout the several views, FIG. 1 is a plan view illustration of a Minimally Invasive Robotic Surgical (MIRS) system 10, typically used for performing a minimally invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The MIRS system 10 can further include a Patient Side Cart 22 (surgical robot) and an Electronics Cart 24. The Patient Side Cart 22 can manipulate at least one removably coupled tool assembly 26 (hereinafter simply referred to as a "tool") through a minimally invasive incision in the body of the Patient 12 while the Surgeon 18 views the surgical site through the Console 16. An image of the surgical site can be obtained by an endoscope 28, such as a stereoscopic endoscope, which can be manipulated by the Patient Side Cart 22 to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient Side Cart 22, and replace it with another tool 26 from a tray 30 in the operating room.

Figure 2:
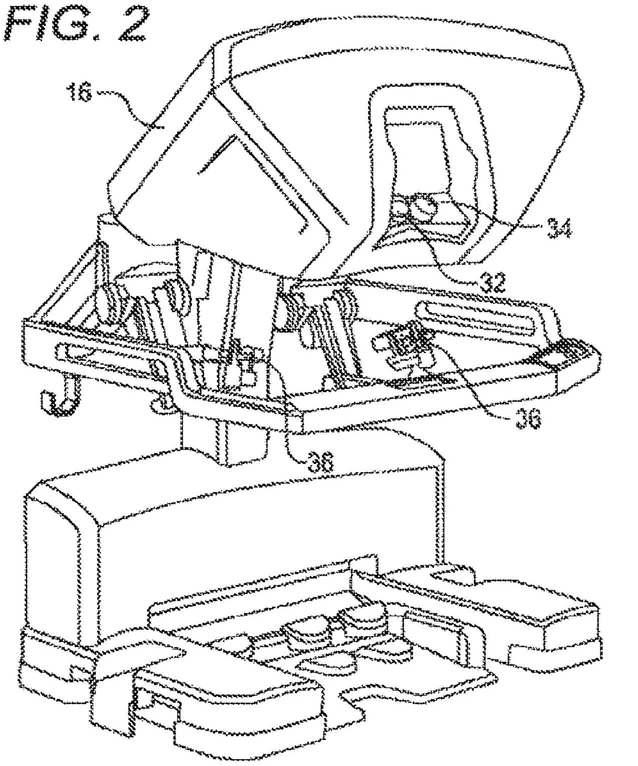
FIG. 2 is a perspective view of a surgeon's control console for a telesurgically controlled surgery system, in accordance with many embodiments.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1) to manipulate one or more tools. The input control devices 36 can provide the same degrees of freedom as their associated tools 26 (shown in FIG. 1) to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures.

Figure 3:
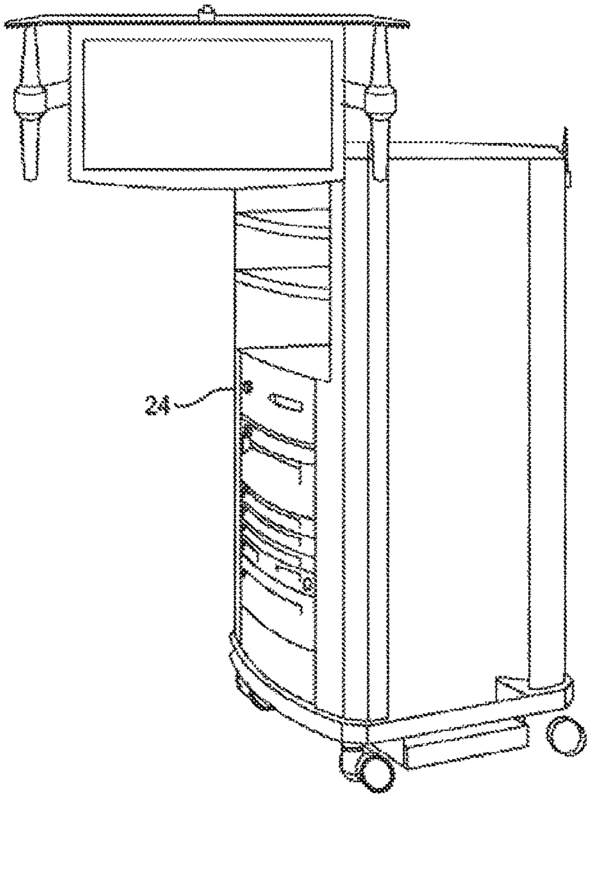
FIG. 3 is a perspective view of a telesurgically controlled surgery system electronics cart, in accordance with many embodiments.

FIG. 3 is a perspective view of the Electronics Cart 24. The Electronics Cart 24 can be coupled with the endoscope 28 and can include a processor to process captured images for subsequent display, such as to a Surgeon on the Surgeon's Console, or on another suitable display located locally and/or remotely. For example, where a stereoscopic endoscope is used, the Electronics Cart 24 can process the captured images to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

Figure 4:
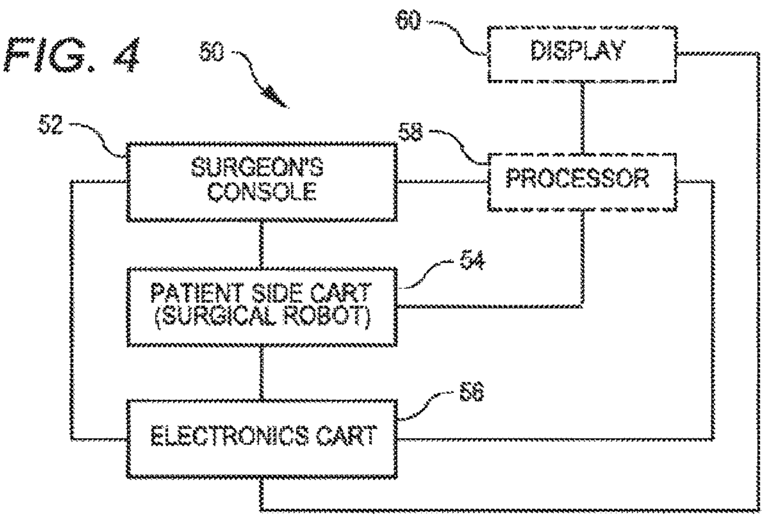
FIG. 4 diagrammatically illustrates a telesurgically controlled surgery system, in accordance with many embodiments.

FIG. 4 diagrammatically illustrates a robotic surgery system 50 (such as MIRS system 10 of FIG. 1). As discussed above, a Surgeon's Console 52 (such as Surgeon's Console 16 in FIG. 1) can be used by a Surgeon to control a Patient Side Cart (Surgical Robot) 54 (such as Patient Side Cart 22 in FIG. 1) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination the Electronics Cart 56 and the processor 58, which can be coupled together to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Figure 5A:
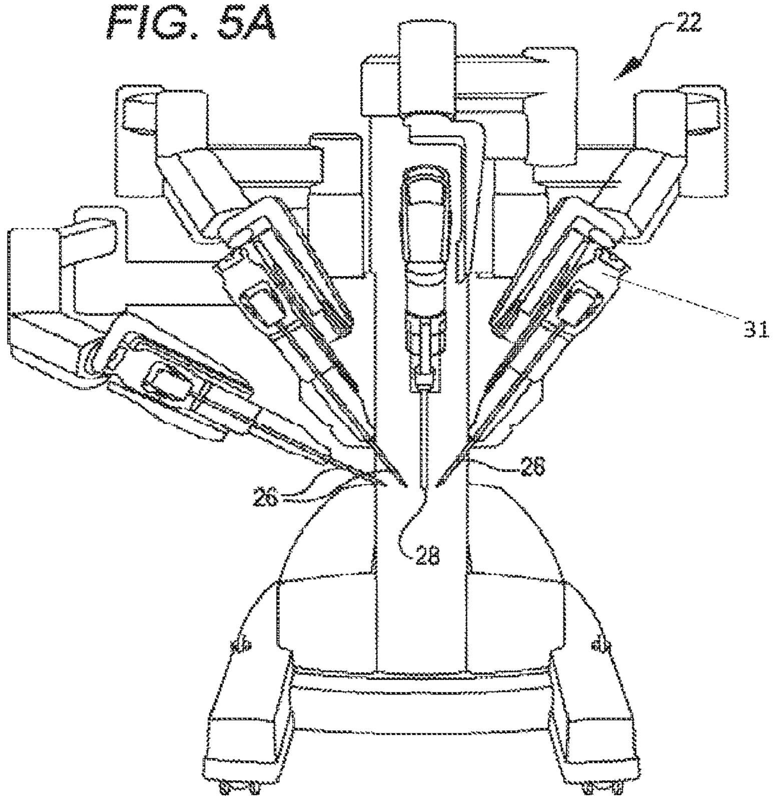
FIG. 5A is a partial view of a patient side cart of a telesurgically controlled surgery system, in accordance with many embodiments.
Figure 5B:
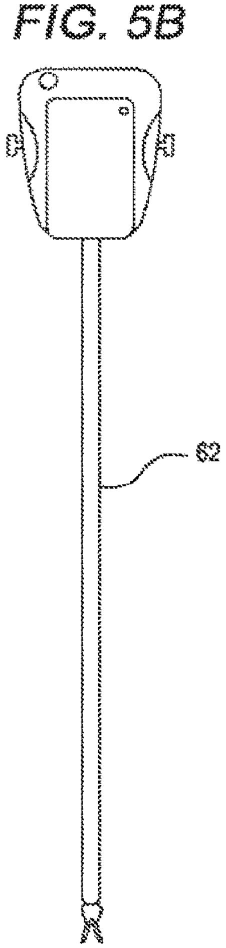
FIG. 5B is a front view of a telesurgically operated surgery tool, in accordance with many embodiments.

FIGS. 5A and 5B show a Patient Side Cart 22 and a surgical tool 62, respectively. The surgical tool 62 is an example of the surgical tools 26. The Patient Side Cart 22 shown provides for the manipulation of three surgical tools 26 and an imaging device 28, such as a stereoscopic endoscope used for the capture of images of the site of the procedure. Manipulation is provided by robotic mechanisms having a number of robotic joints. The imaging device 28 and the surgical tools 26 can be positioned and manipulated through incisions in the patient so that a kinematic remote center is maintained at the incision to minimize the size of the incision. Images of the surgical site can include images of the distal ends of the surgical tools 26 when they are positioned within the field-of-view of the imaging device 28.

Each tool 26 is detachable from and carried by a respective instrument holder 31, which is located at the distal end of one or more of the robotic joints. The instrument holder 31 provides a moveable platform for moving the entirety of a tool 26 with respect to the Patient Side Cart 22, via movement of the robotic joints. The instrument holder 31 also provides power to operate the tool 26 using one or more mechanical and/or electrical interfaces. An example of such a carriage assembly is found at U.S. Patent Publication No. US 2013/0325034, which is incorporated by reference.

Figure 6:
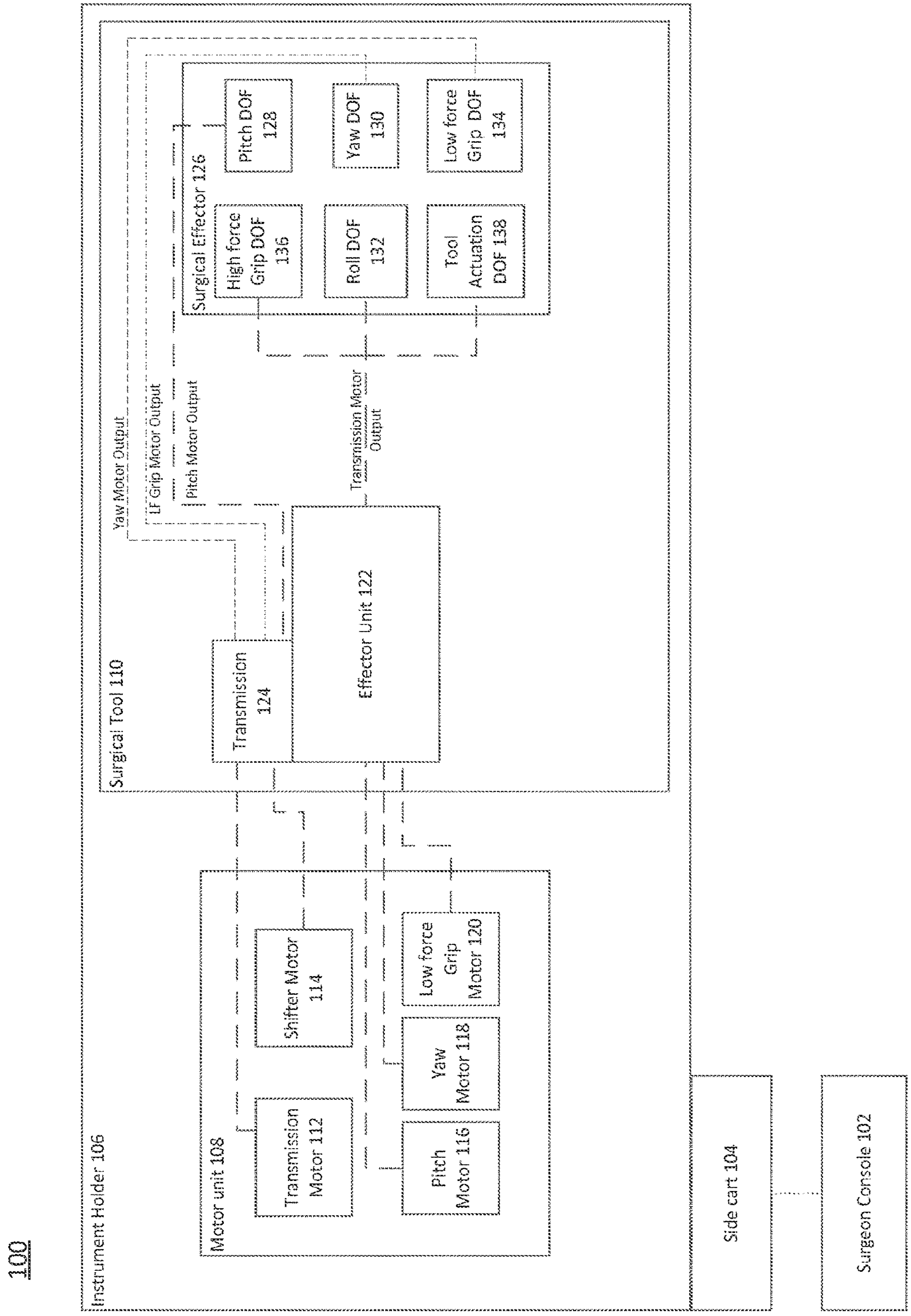
FIG. 6 is a simplified schematic diagram of a telesurgically controlled surgery system surgical system, in accordance with many embodiments.

FIG. 6 is a simplified schematic diagram of a telesurgically controlled surgery system surgical system 100. The surgical system 100 includes a surgeon console 102, which for example can be the Surgeon's Console 52. The surgeon console 102 drives a patient side cart 104, which for example can be the Patient Side Cart 22. The patient side cart 104 includes an instrument holder 106, which for example can be the instrument holder 31.

The instrument holder 106 includes two detachable platforms, the first being a motor unit 108 and the second being a tool 110. The motor unit 108 is a carriage assembly that holds 5 motors. In some embodiments only 5 motors are used, while in other embodiments more or less than 5 motors can be used. Here, the motor unit 108 includes a plurality of motors, which can be assigned to different mechanisms/components. Here, the motor unit 108 includes a transmission motor 112, shifter motor, 114, pitch motor 116, yaw motor 118, and low-force grip motor 120, although these motors can be used for different purposes depending on the attached instrument. Generally, each motor is an electric motor that mechanically and electrically couples with corresponding inputs of the instrument holder.

The tool 110 for example, can be the tool 26 described above. An example of a tool usable as tool 110 is at Int'l. Pub. No. WO 2011/060318, which is incorporated by reference. Here, the tool 110 is an elongated effector unit 122 that includes three discrete inputs that each mechanically couple with the pitch motor 116, yaw motor 118, and a low-force grip motor 120 by way of the instrument holder 106. The tool 110 also includes a transmission 124, which mechanically couples with the transmission motor 112 and the shifter motor 114.

A surgical end effector 126 is located at the distal end of the effector unit 122. The surgical end effector 126 and effector unit 122 are connected by way of a moveable wrist. An example of such a wrist is shown at U.S. Patent Publication No. US 2011/0118709, which is incorporated by reference herein. In simplistic terms, the surgical end effector can be characterized by a plurality of discrete but interrelated components, with each component providing a degree of freedom (DOF) for the surgical end effector 126. As used herein, a DOF is one or more interrelated components for affecting a corresponding movement. The DOFs endow the surgical end effector 126 with different modes of operation that can operate concurrently or discretely. For example, the wrist enables the surgical end effector 126 to pitch and yaw with respect to the instrument holder 106, and accordingly includes a pitch DOF 128 and a yaw DOF 130. The surgical end effector 126 also includes a roll DOF 132 rotating surgical end effector about an elongated axis.

The surgical end effector 126 may include a clamping and cutting mechanism, such as a surgical stapler. An example of such a clamping mechanism is shown at U.S. Patent Publication No. U.S. Ser. No. 12/945,541, filed Nov. 12, 2010, which is incorporated by reference. The clamping mechanism can grip according to two modes, and accordingly includes two DOFs. A low-force DOF 132 (e.g., a cable actuated mechanism) operates to toggle the clamp with low force to gently manipulate tissue. The low-force DOF 132 is useful for staging the surgical end effector for a cutting or stapling operation. A high-force DOF 134 (e.g., a lead screw actuated mechanism) operates to further open the clamp or close the clamp onto tissue with relatively high force, for example, to tourniquet tissue in preparation for a cutting or stapling operation. Once clamped, the surgical end effector 126 employs a tool actuation DOF 138 to further affect the tissue, for example a stapling, cutting, and/or cauterizing device.

As shown, the pitch motor 116, yaw motor 118, and low force grip motor 120 drive the pitch DOF 128, yaw DOF 130, and low force grip DOF 139, respectively. Accordingly, each of the pitch DOF 128, yaw DOF 130, and low force grip DOF 139 is discretely paired with a motor, and can operate independently and concurrently with respect to other DOFs.

However, the high force DOF 126, roll DOF 132, and tool actuation DOF 138 share a single input with the transmission motor 112, via the transmission. Accordingly, only one of the high force DOF 126, roll DOF 132, and tool actuation DOF 138 can operate at one time, since coupling with the transmission motor occurs discretely. The shifter motor 114 is actuated to shift output of the transmission motor 112 between the high force DOF 126, roll DOF 132, and tool actuation DOF 138. Accordingly, the transmission 124 advantageously allows a greater amount of DOFs than an arrangement where each motor is dedicated to a single DOF.

II. Exemplary Transmission

Embodiments of invention relate to a system and method to control the 6 degrees of freedom (6 DOFs) of a stapler instrument with the 5 inputs allowable from a motor carriage. It takes one of the five inputs to use as a shifter, which then allows another input to be selectively engaged to three different stapler DOFs. The six DOFs of a stapler instrument can include wrist roll, wrist pitch, wrist yaw, low-force grip (toggle), high-force grip (clamp), and tool actuation (stapler fire). Wrist pitch, yaw, and low-force grip may be cable actuated, while roll, clamp, and fire are driven by independent sets of coaxial gears. In use, the transmission can include three main modes: roll, clamp/unclamp, and fire. Wrist rotation, pitch, yaw, and low-force grip are all under active servo control, and the high-force grip and fire DOFS are coupled to the roll axis.

In many embodiments, the driven input is selectively coupled to wrist roll, clamp, and/or fire. This is done through the use of idler gears that can be rotated in and out of engagement with the appropriate stapler DOF. Additionally, there is a method to lock each DOF to ground through the use of a lever arm. These lever arms are controlled by the shifting input, which can be a camshaft with the appropriate number and shapes of lobes. During a roll movement of the wrist, it is necessary for the clamp and fire input rings to rotate along with the roll gear. Because of this constraint, the gear ratios between the instrument input and the input rings and roll gear are all the same. That way, during the following state, all of the rings/gears are engaged, and therefore rotate together, so the fire and high-force grip drive shafts do not turn with respect to the wrist. The system can be configured so that all transitions move only one function at a time. This way all transitions are testable for safety. When transitioning out of following, the roll gear is locked. To avoid the necessity of the wrist needing to be positioned such that the roll gear is aligned with the teeth of the locking arm, there is a secondary friction lock on this DOF.

Figure 7A:
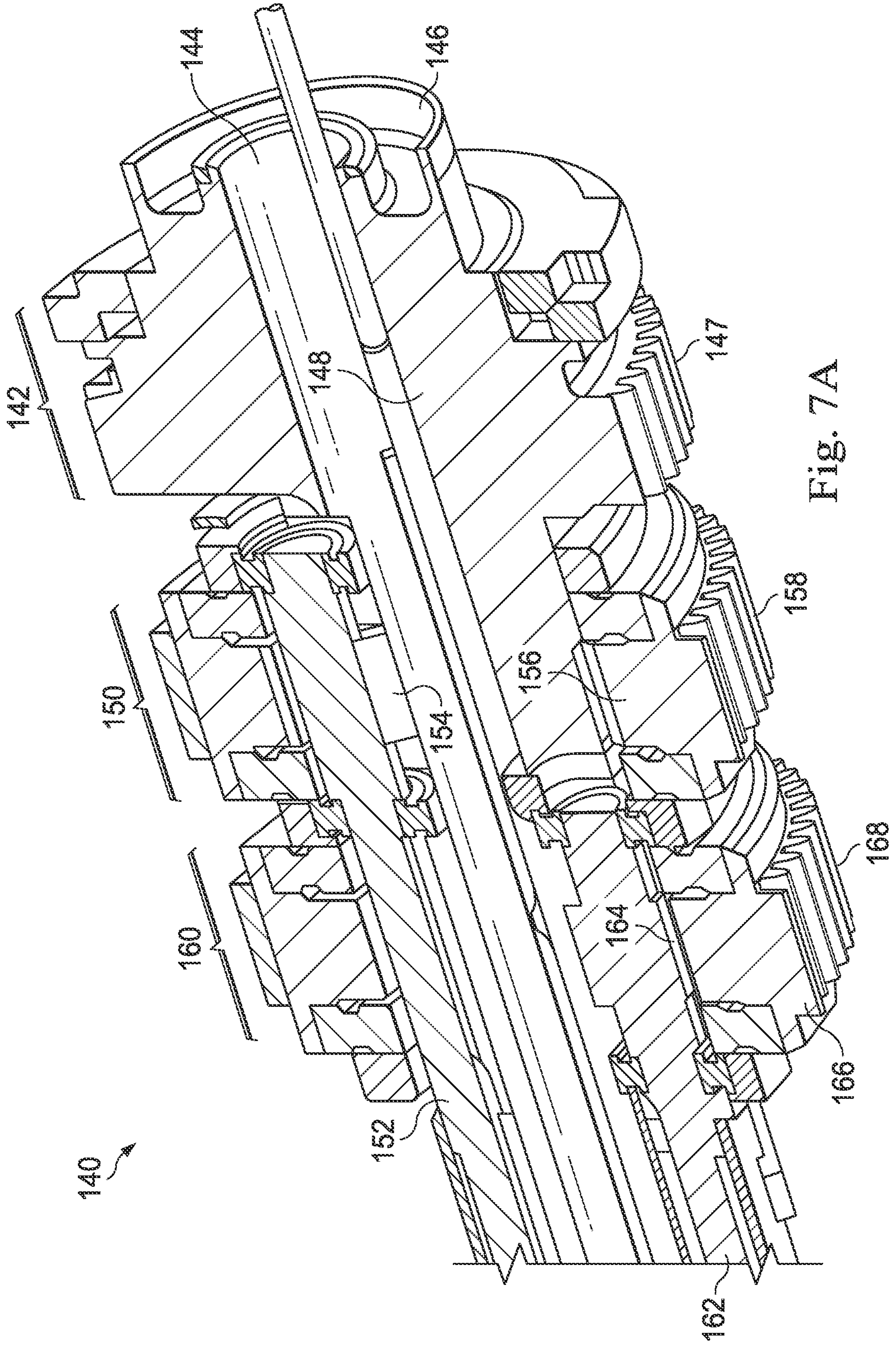
FIGS. 7A-7C are longitudinal and axial cross-sections of a transmission assembly of a telesurgically operated surgery tool, in accordance with many embodiments.
Figure 7B:
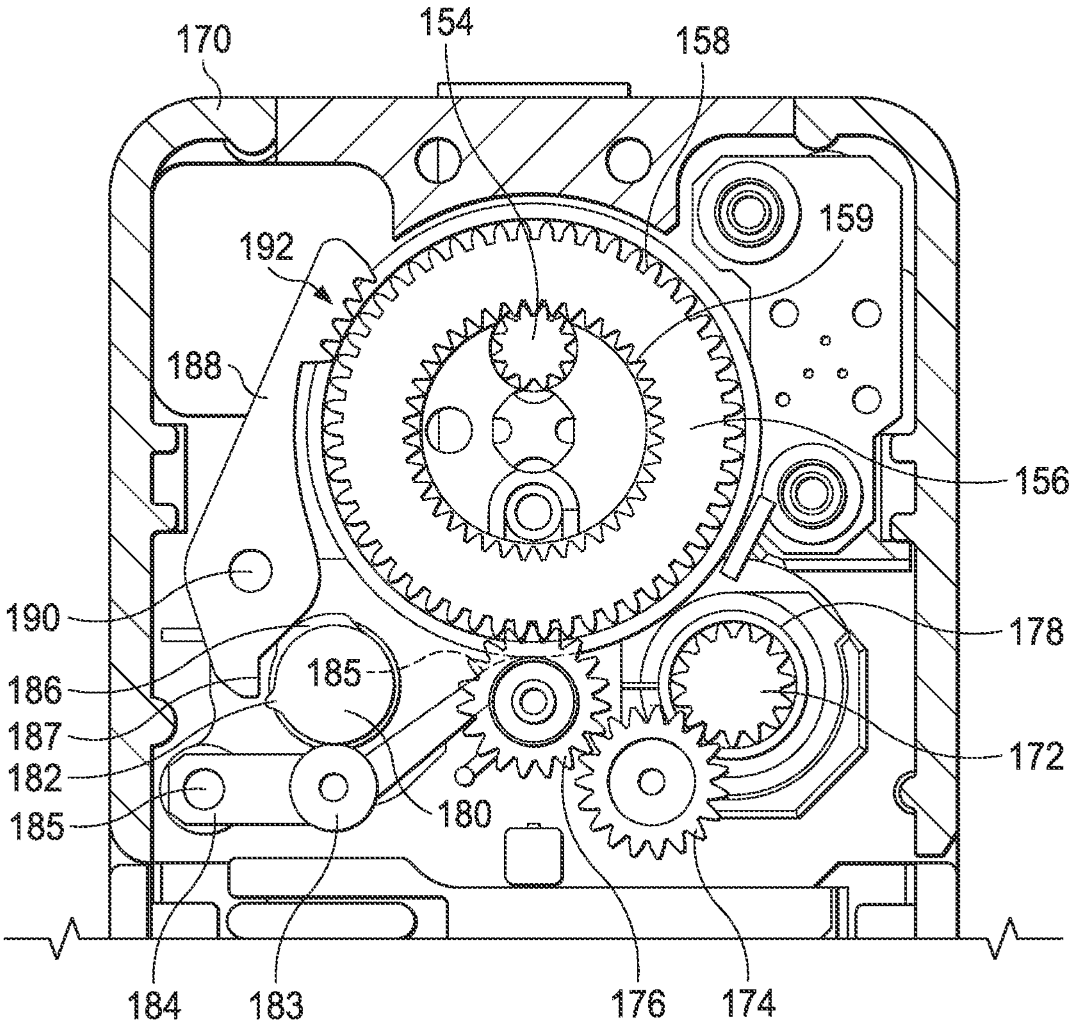

FIGS. 7A and 7B respectively show longitudinal and axial cross-sections of a transmission assembly 140. The transmission includes a gear train for each of the high force DOF 126, roll DOF 132, and tool actuation DOF 138.

A. First Gear Train

With attention to FIG. 7A, a first gear train 142 is located at the proximal end of the transmission assembly 140. The first gear train 142 drives the roll DOF 132 by axially rotating a main shaft 144. The main shaft 144 includes an axial passageway 146 for routing control cables to the surgical end effector 126. The main shaft 144 is directly rotated by driving external gear teeth 147 of a proximal gear 148.

B. Second Gear Train

A second gear train 150 is located directly adjacent to the first gear train 142, at a mid-portion of the transmission assembly 140. The second gear train 150 drives the high force grip DOF 126 by rotation of a middle shaft 152 with respect to the main shaft 144. The middle shaft 152 is held by the main shaft 144 and accordingly is rotated with the main shaft 144. Put another way, the axis of rotation of the middle shaft 152 can orbit about the axis of rotation of the main shaft 144.

The middle shaft 152 is directly connected to a middle internal gear 154, which in turn is driven by internal gear teeth (not shown in this view) of a middle gear 156. The middle gear 156 also includes external gear teeth 158 for directly driving the middle gear 156, ultimately by way of the transmission motor 112. The external gear teeth 158 of the middle gear 156 are configured identically to the external gear teeth 147 of the proximal gear 148. Accordingly, if driven synchronously, assuming identical input gears, there is no relative movement between the middle gear 156 and the proximal gear 148, and accordingly the middle shaft 152 is not driven.

An external portion of the main shaft 144 holds the middle gear 156 by way of a bearing. In a first disengaged state of the second gear train 150, the middle gear 156 (together with a distal gear 166 described below) can be configured to synchronously rotate with the main shaft 144 when both the middle gear 156 and are and proximal gear 148 are synchronously engaged with the transmission motor 112. In the first disengaged state, rotation of the middle gear 156 does not result in rotation of the middle internal gear 154, since the middle gear 156 is not allowed to roll with respect to the main shaft 144. Put another way, in the first disengaged state, the middle gear 156 clocks with the main shaft 144, and thus cannot move asynchronously with respect to the main shaft 144 to move the middle shaft 152. As discussed further below, the second gear train 150 includes a second disengaged state, in which the middle gear 156 is physically disengaged from the transmission motor 112 and physically locked, and thereby cannot rotate cannot drive the middle internal gear 154.

In an engaged state of the second gear train 150 (with the transmission motor 112), the proximal gear 148 and main shaft 144 are locked and therefore cannot rotate. Thus, the axis of rotation of the middle internal gear 154 cannot orbit about the axis of rotation of the main shaft 144. However, the middle internal gear 154 can spin about its own axis of rotation. Accordingly, in the engaged state, the middle gear 144 rotates with respect to the main shaft 144, and thereby drives the middle internal gear 154, ultimately by way of the transmission motor 112.

C. Third Gear Train

A third gear train 160 is located at a distal portion of the transmission assembly 140, and is largely configured in the same manner as the second gear train 150. The third gear train 160 drives the tool actuation DOF 138 by rotation of a distal shaft 162 with respect to the main shaft 144. The distal shaft 162 is held by the main shaft 144 and accordingly rotates with the main shaft 144. In the general manner as the second gear train 150, the axis of rotation of the distal shaft 162 can orbit about the axis of rotation of the main shaft 144.

The distal shaft 162 is directly connected to a distal internal gear 164, which in turn is driven by internal gear teeth (not shown in this view) of a distal gear 166. The distal gear 166 also includes external gear teeth 168 for directly driving the distal gear 166, ultimately by way of the transmission motor 112. The external teeth 168 of the distal gear 162 are configured in the same manner as the external gear teeth 147 of the proximal gear 148, as well as the external gear teeth 158 of the middle gear 156. Accordingly, when driven synchronously, there is no relative movement between the distal gear 166, middle gear 156 and proximal gear 148.

An external portion of the main shaft 144 holds the distal gear 166 by way of a bearing. In a first disengaged state of the third gear train 160, the distal gear 166 (together with the middle gear 156) can be configured to synchronously rotate with the main shaft 144 when both the distal gear 166 and are and proximal gear 148 are synchronously engaged with the transmission motor 112. In the first disengaged state, rotation of the distal gear 166 does not result in rotation of the distal internal gear 164, since the distal gear 166 is not allowed to roll with respect to the main shaft 144. Put another way, in the first disengaged state, the distal gear 166 clocks with the main shaft 144, and thus cannot move asynchronously with respect to the main shaft 144 to move the distal shaft 162. As discussed further below, the third gear train 160 includes a second disengaged state, in which the distal gear 166 is physically disengaged from the transmission motor 112 and physically locked, and thereby cannot rotate cannot drive the distal internal gear 164.

In an engaged state of the third gear train 160 (with the transmission motor 112), the proximal gear 148 and main shaft 144 are locked and therefore cannot rotate. In this manner, the axis of rotation of the distal internal gear 164 cannot orbit about the axis of rotation of the main shaft 144. However, the distal internal gear 164 can spin about its own axis of rotation. Accordingly, in the engaged state, the distal gear 166 rotates with respect to the main shaft 144, and thereby drives the distal internal gear 164, ultimately by way of the transmission motor 112.

D. Gear Train Construction

With attention to FIG. 7B, a representative cross section of the second gear train 150 is shown. The first gear train 142 and third gear train 160 are configured in the same manner, accordingly, the following description applies in kind. However, the proximal gear 148 of the first gear train 142 does not include inner gear teeth and internal gear as shown, since the proximal gear 148 turns the main shaft 144.

A greater housing 170 of the surgical tool 110 holds the transmission assembly 140. The transmission motor 112 drives a first input gear 172, which is shared for each of the gear trains. The first input gear 172 is meshed with an idler gear 174, which in turn meshes with a second input gear 176 that meshes with the middle gear 156. The second input gear 176 is on an arm (not shown) that rotates about the first input gear 172. As shown, the second input gear 176 is positioned at the upward portion of the track, and thereby meshed with the middle gear 156. The second input gear 176 can be moved to disengage the second input gear 176 from the middle gear 156. An input spring 176 is loaded between the second input gear 176 and housing 170 to bias the second input gear 176 against the middle gear 156.

A camshaft 180 is disposed along the gear trains. The camshaft 180 generally includes two cam lobes per drive chain. The lobes rotate to engage and disengage a DOF mechanism with a gear train.

A first cam lobe 182 rotates to engage a surface 183 of a rocker arm 184. The rocker arm 184 is moveable about a rocker pivot 186. The rocker arm 184 extends to engage the second input gear 176 at a hooked portion 185 of the rocker arm. When a low portion of the first cam lobe 182 is engaged with the rocker arm 184, the second input gear 176 is engaged with the middle gear 156 as shown.

When a high portion of the first cam lobe 182 engages the surface 183 of the rocker arm 184, the rocker arm 184 is moved downwardly about the rocker pivot 186. Due to the engagement of the rocker arm 184 and the second input gear 176, this downward motion disengages the second input gear 176 from the middle gear 156. Accordingly, in this position of the first cam lobe 182, power applied to the first input gear is not translated to the middle gear 156.

A second cam lobe 186 rotates to engage a surface 187 of a locker arm 188, which pivots about locker arm pivot 190. The locker arm 188 includes a toothed portion 192 that can be moved to mesh the toothed portion 192 with the middle gear 156. A locker spring 194 is loaded between the locker arm 188 and housing 170 to bias the toothed portion 192 away from the middle gear 156.

When a low portion of the second cam lobe 186 engages the surface 187 of the locker arm 188, the toothed portion 192 is moved away from the middle gear 156, as shown. Accordingly, in this position the middle gear 156 is unlocked and allowed to rotate.

Figure 7C:
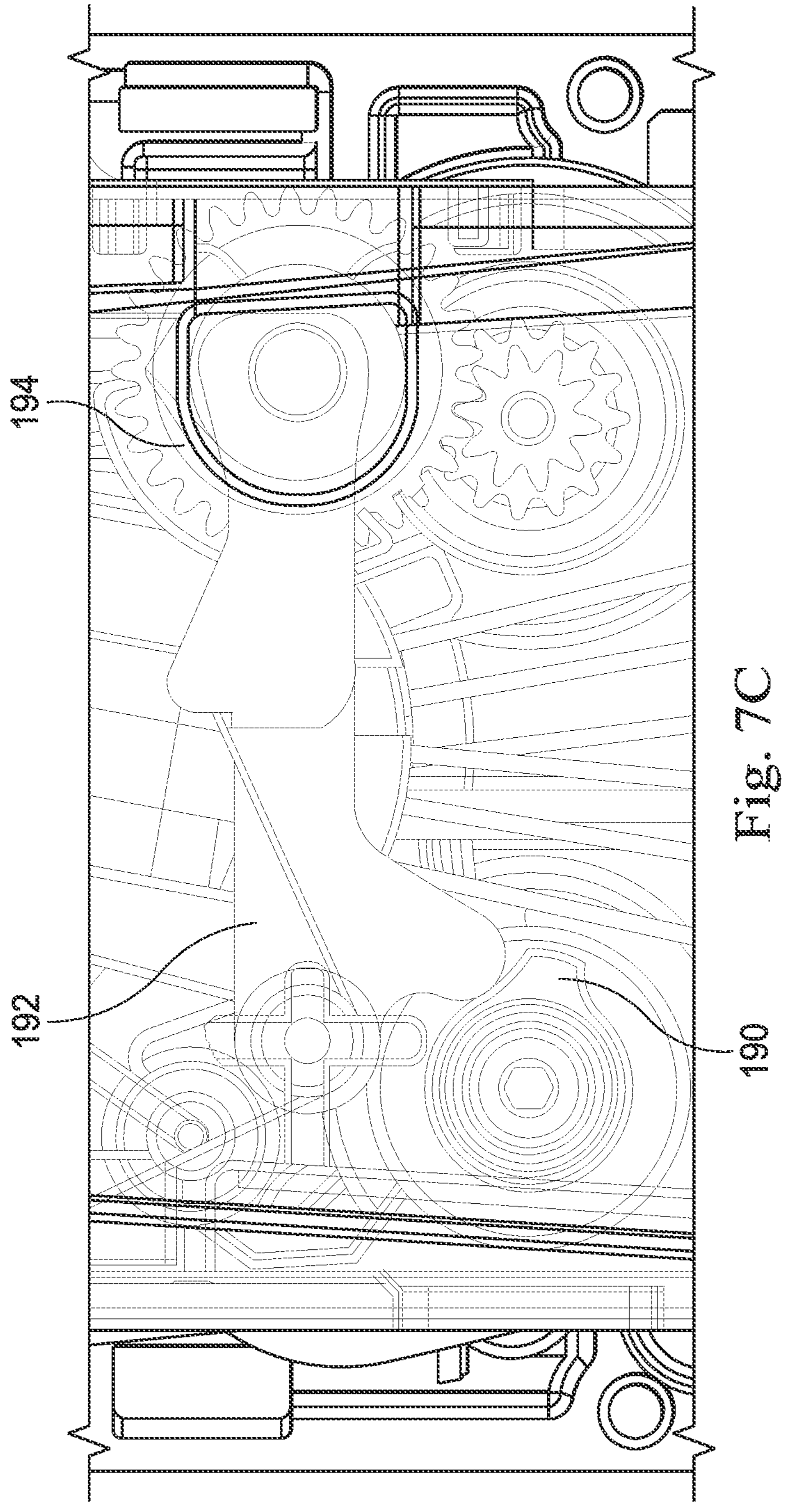

In the case of a system failure while the stapler is clamped on tissue, a manual unclamp feature is provided. In some embodiments, this can be accomplished by the user manually rotating the camshaft 180 to the high force grip DOF state, as described below. As shown in FIG. 7C, an interlock cam 190 is moveable to a high state to move an interlock flag 192 that rotatable and connected to a one-way clutch 194, which ultimately interfaces with the middle shaft 152. At the clamp state, an interlock flag 192 provides the user access to drive the middle shaft 152 via the one-way clutch 194 in a direction that only allows for the jaws to be unclamped.

III. Transmission Shifting Method

When a high portion of the second cam lobe 186 engages the surface 187 of the locker arm 188, the toothed portion 192 is moved to engage the middle gear 156. This position locks the middle gear 156 with the locker arm 188, and accordingly, the middle gear 156 cannot move. One purpose of locking the middle gear 156 is to lock the last position of the high force grip DOF into a locked state. Generally, each gear train is locked in a similar manner, thus unwanted movement.

Figure 8:
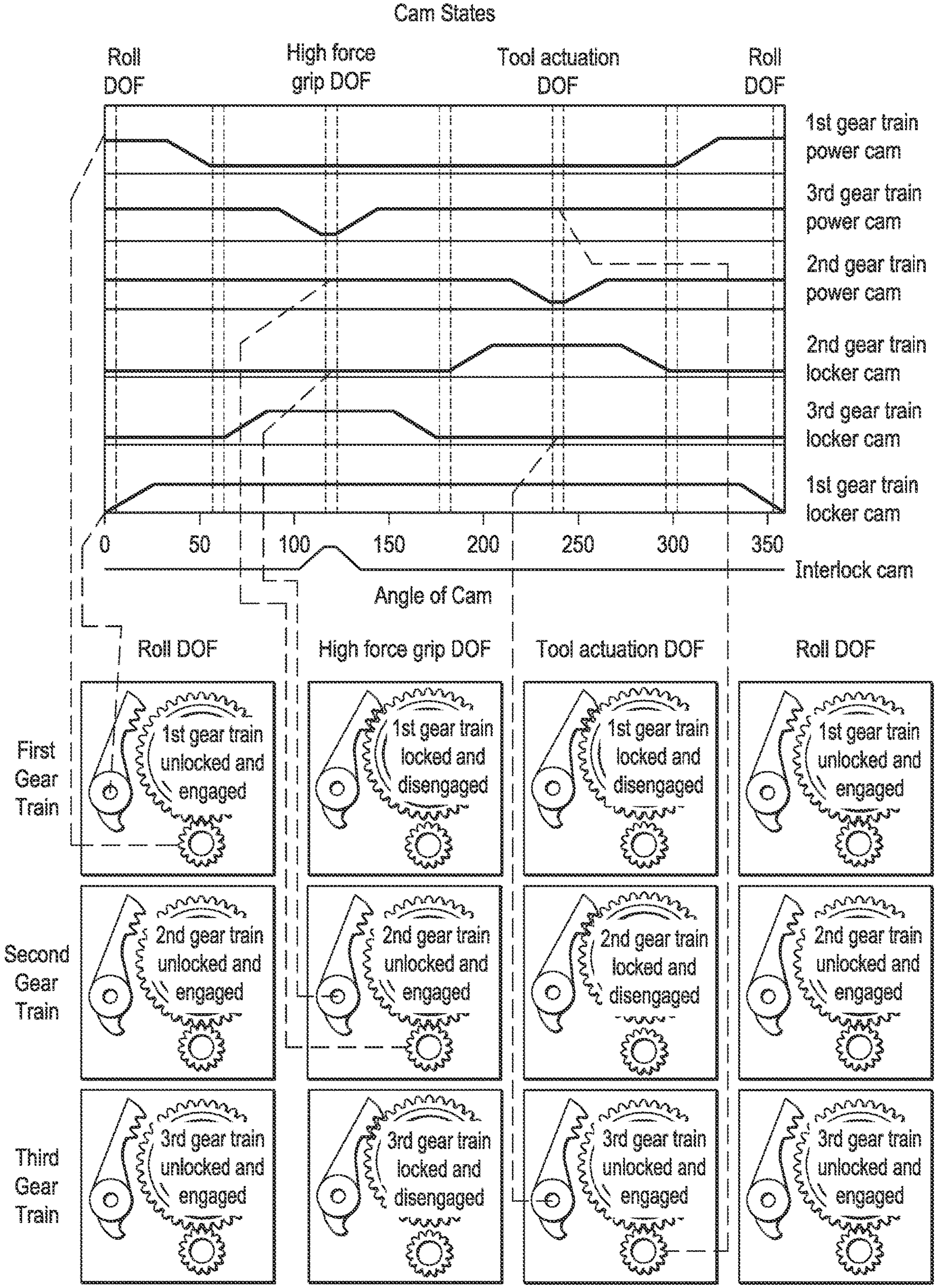
FIG. 8 shows a cam state chart for operation of the of a transmission assembly of a telesurgically operated surgery tool, in accordance with many embodiments.

The camshaft 180 is configured to operate the gear trains in harmony, which is achieved through camshaft timing. FIG. 8 shows a cam state chart for operation of the transmission 140. As discussed previously, the gear trains share a common camshaft, which for example is the camshaft 180 shown in FIG. 7B. The camshaft 180 provides each gear train with at least two lobes, e.g., the first cam lobe 182 and second cam lobe 186 operate with the second gear train 150. However, some gear trains can include more lobes. For example, in some embodiments, the first gear train includes a third lobe to operate a friction lock. And as shown in FIG. 7C, additional lobes can be included as safely mechanisms to back drive DOFs in case of a system failure.

Generally, for each gear train, one cam lobe is operable to control power engagement and the other cam lobe is operable to lock the gear train. Accordingly, each gear train is operated by a power cam and a locker cam. In simplistic terms, each cam has a low state and a high state, with transitions ramps in between. The duration of each low and high state is based on the desired duration of operation of an object being lifted (e.g., the locker arm 188 and the rocker arm 184.

A. Cam State for First Transmission Mode

The cam state chart shows the low and high state for each cam over 360 degrees of rotation. At 0 and 360 degrees of rotation, the transmission 140 is configured to supply power for operation of the roll DOF 132. As shown, the power cam for each gear train is at a high state and the locker cam for each gear train is at a low state. Accordingly, the first gear train 142 is unlocked and engaged with the transmission motor 112. In this manner, the locker arm of the first gear train 142 is disengaged from the proximal gear 148 and the second input gear is engaged with the proximal gear 148. The second gear train 150 and the third gear train 160 are also unlocked, and the middle gear 156 and distal gear 166 remain in contact with the transmission motor.

As described above, during engagement of the roll DOF 132, the middle gear 156 and distal gear 166 are required to rotate in sync with the proximal gear 148, since the middle internal gear 154 and distal internal gear 164 are held within and rotate with the shaft 144. In this manner, relative movement is avoided between the middle gear 156/middle internal gear 154 and the distal gear 166/distal internal gear 164, thereby preventing operation of the middle shaft 152 and distal shaft 162. Accordingly, although the middle gear 156 and distal gear 166 remain engaged with the transmission motor 112, and thus are turned during a roll operation, the second gear train 150 and the third gear train 160 do not operate respective DOFs.

B. Cam State for Second DOF

At approximately 120 degrees of rotation of the camshaft 180, the transmission is configured to provide power to the high force grip DOF 136. Here, the power cams of the first gear train 142 and the third gear train 160 are at lows states and the power cam of the second gear train 150 is at a high state. In this manner, the second input gears of the first gear train 142 and the third gear train 160 are respectively disengaged from the proximal gear 148 and the distal gear 166, while the second input gear of the second gear train 150 is engaged with the middle gear 156. Thus, only the middle gear 156 receives power from the transmission motor 112. The locker cams of the first gear train 142 and the third gear train 160 are at high states and the power cam of the second gear train 150 is at a low state. In this manner, the locker arms of the first gear train 142 and the third gear train 160 are respectively engaged with the proximal gear 148 and the distal gear 166, while the locker arm of the second gear train 150 is disengaged from the middle hear 156. In addition, an interlock cam is driven to a high state, as described above with reference to FIG. 7C. This allows user access to a interlock flag to manually back drive the second gear train in case of a system failure.

C. Cam State for Third DOF

At approximately 240 degrees of rotation of the camshaft 180, the transmission is shifted to provide power to the tool actuation DOF 138. Here, the power cams of the first gear train 142 and the second gear train 150 are at lows states and the power cam of the third gear train 160 is high. In this manner, the second input gears of the first gear train 142 and the second gear train 150 are respectively disengaged from the proximal gear 148 and the middle gear 156, while the second input gear of the third gear train 160 is engaged with the distal gear 166. Thus, only the distal gear 166 receives power from the transmission motor 112. The locker cams of the first gear train 142 and the second gear train 150 are at high states and the locker cam of the third gear train 160 is at a low state. In this manner, the locker arms of the first gear train 142 and the second gear train 150 are respectively engaged with the proximal gear 148 and the middle gear 156, while the locker arm of the third gear train 160 is disengaged from the distal gear 166. Thus, only the distal gear 166 is free to turn.

Figure 9:
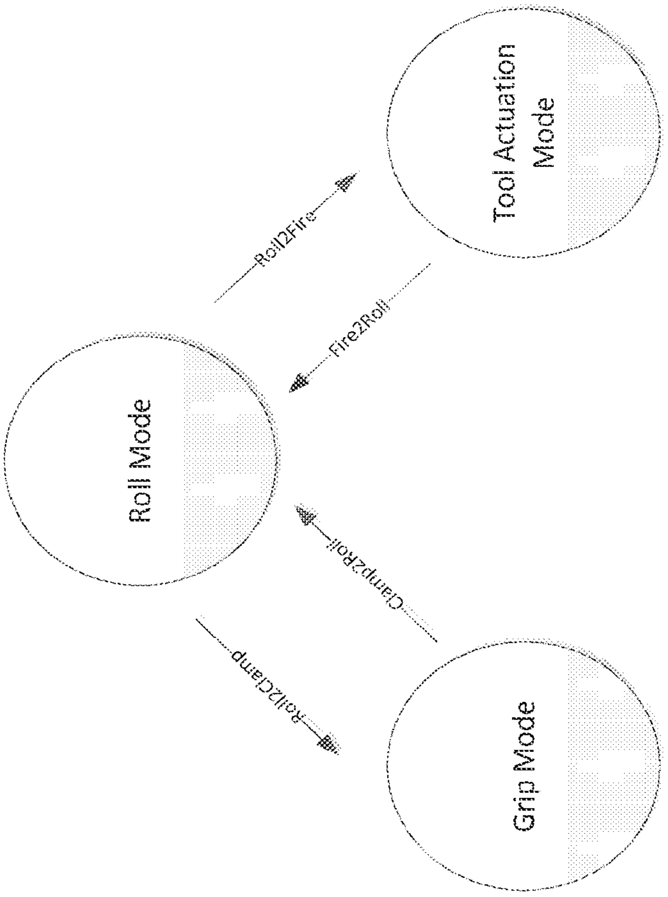
FIG. 9 shows a high-level flow chart for shifting operational modes of a transmission assembly of a telesurgically operated surgery tool, in accordance with many embodiments.
Figure 10:
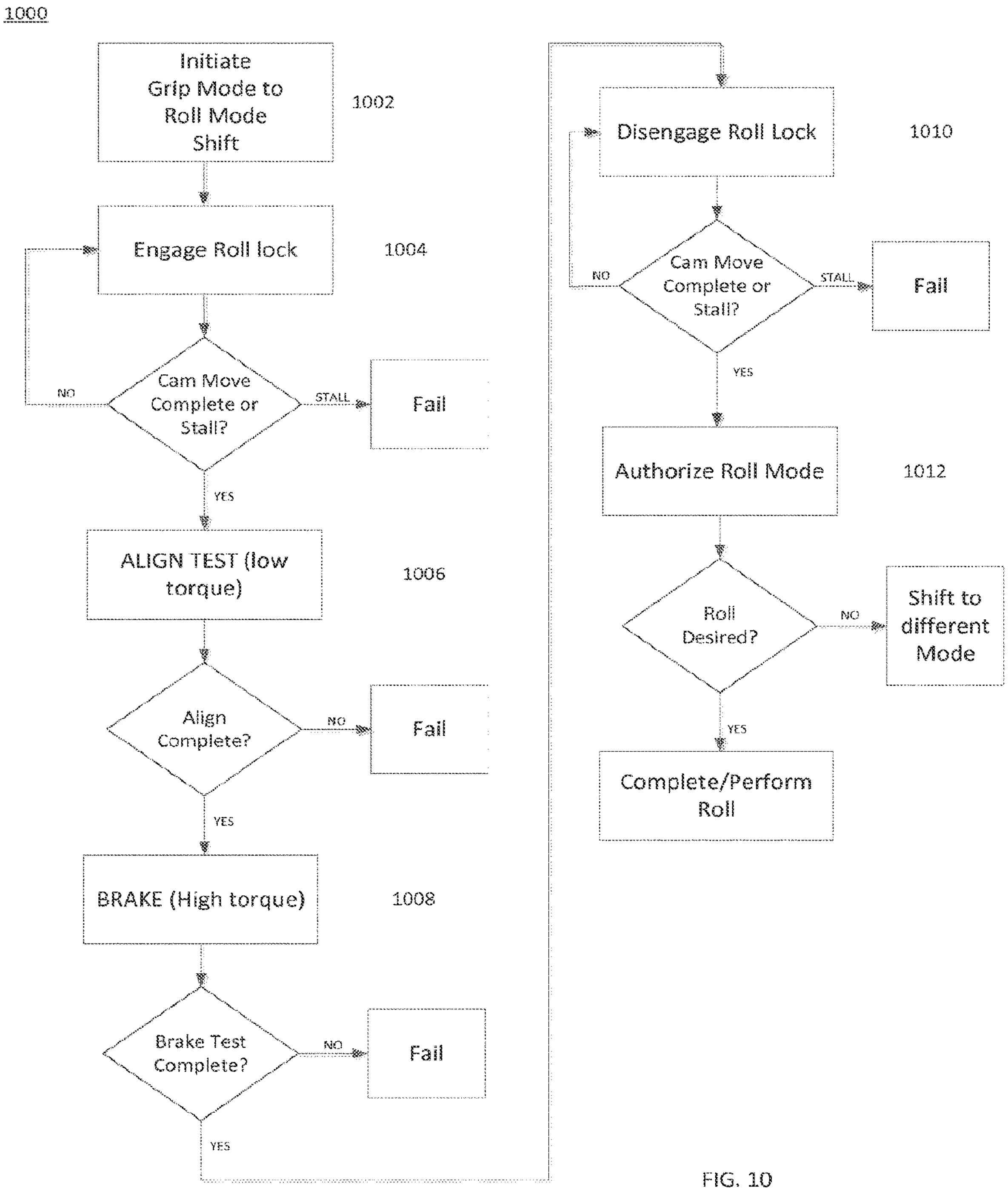
FIG. 10 shows a flow chart for shifting operational modes of a transmission assembly of a telesurgically operated surgery tool between first and second operational modes, in accordance with many embodiments.

FIG. 9 shows a high-level diagram of different operational modes of the transmission 140, i.e., shifting output between the first gear train 142 (Roll Mode), second gear train 150 (Grip Mode), and the third gear train 160 (Tool Actuation Mode). Between each mode, a shifting algorithm is specified for each particular mode-to-mode shift. For some surgical instruments transitioning between modes can be critical with respect to the rolling position of an elongated shaft of the instrument, since the roll position effects position of the surgical instrument as a whole. Occasionally, there is backlash in the gears in the stapler instrument transmission. Over time, the motion from the small backlash causes the roll/clamp/fire orientation/position to drift from its reference point. To compensate for the slight backlash motion, the initial roll position may be defined as being against one side of the gear. As part of the shifting algorithm the gears are biased (moved) to this position, so that the roll positions are consistent with reference to backlash in the gears. This helps improves shift accuracy positions, and can be done for the other output shafts as well. The camshaft 180 has to manage braking for roll, grip, and tool actuation functions. It is important that the camshaft 180 is in the right position for roll, grip, and tool actuation before activating these features. In some embodiments, there is a roll encoder engaged with the camshaft 180 that allows software to monitor the cam position, and the roll, grip, and tool actuation modes are only enabled when the cam is sensed as being in its correct orientation. An example of shifting from the Grip Mode to the Roll Mode is shown at FIG. 10. However, this method is relatively generic and is applicable to shifting between other modes of the transmission 140.

At operation 1002, a controller (e.g., a processor of the side cart 104) receives a command (e.g. from the surgeon console 102) to shift from the Grip Mode (engagement of the second gear train 150 to transmission motor 112) to the Roll Mode (engagement of the first gear train to transmission motor 112). Hence, the controller at operation 1004 drives the shifter motor 114 to move the camshaft 180 and thereby engage the proximal gear 148 with the transmission motor 112. During this operation, the controller waits for the camshaft 180 to move and periodically checks to determine whether the movement is complete or has stalled out, due to for example, gear tooth misalignment. If it is determined that the operation has stalled, then the shift is aborted.

After the controller has determined that the proximal gear 148 is locked, the controller performs an Align Test at operation 1006. For the Align Test, the proximal gear 148 is driven against the locker arm using the transmission motor 112 to determine that the proximal gear 148 and camshaft 180 are properly aligned, i.e., at a predetermined park position. In this operation, the transmission motor 112 is driven using a relatively low torque in an attempt to stall movement of the proximal gear 148 under the relatively low torque. If the movement is stalled, then the controller determines that the proximal gear 148 is properly aligned. If the movement does not stall, i.e., moves excessively without stalling, controller determines that the proximal gear 148 is not properly aligned, and the shift is aborted.

After the controller has determined that the proximal gear 148 is aligned, the controller performs a Brake Test at operation 1008 to check whether the proximal gear 148 is properly braked before allowing use. For the Brake Test, the proximal gear 148 is driven against the locker arm using a relatively high torque to determine whether the transmission motor 112 becomes magnetically saturated under applied load. If so, this indicates that the proximal gear is properly braked. If the transmission motor 112 is not saturated under the torque, then the Brake Test is halted and the shift is aborted.

At operation 1010, controller drives the shifter motor 114 to move the camshaft 180 and thereby unlock the proximal gear 148. During this operation, the controller waits for the camshaft 180 to move and periodically checks to determine whether the movement is complete or has stalled out. If it is determined that the operation has stalled, then the shift is aborted. If the operation does not stall, then the proximal gear 148 is unlocked and enabled for use at operation 1012. In some cases, although the roll mode is authorized, it is not desired to roll the shaft. Hence, the output of the motor 112 can be shifted to a different gear train, which essentially repeats the method 1000.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method, comprising:

driving, by a motor, a camshaft of a transmission of a telesurgically operated instrument to a first rotational state of a plurality of rotational states, wherein the camshaft defines a longitudinal axis and rotates about the longitudinal axis;

engaging, in the first rotational state, a first input gear of a first effector drivetrain of the transmission with a first gear of the first effector drivetrain via a first power cam of the camshaft; and disengaging, in the first rotational state, a first locker arm of the first effector drivetrain from the first gear via a first locker cam of the camshaft.

2. The method of claim 1, further comprising:

engaging a primary input gear of the transmission with the first effector drivetrain via the first power cam; and engaging an idler gear of the transmission with the primary input gear and the first input gear via the first power cam.

3. The method of claim 1, further comprising:

rotating, by the motor, in the first rotational state, the first power cam and the first locker cam 120 degrees about the longitudinal axis of the camshaft.

4. The method of claim 1, further comprising:

engaging, in the first rotational state, a second input gear of a second effector drivetrain of the transmission with a second gear of the second effector drivetrain via a second power cam of the camshaft; and disengaging, in the first rotational state, a second locker arm of the second effector drivetrain from the second gear via a second locker cam of the camshaft.

5. The method of claim 4, further comprising:

engaging, in the first rotational state, a third input gear of a third effector drivetrain of the transmission with a third gear of the third effector drivetrain via a third power cam of the camshaft; and disengaging, in the first rotational state, a third locker arm of the third effector drivetrain from the third gear via a third locker cam of the camshaft.

6. The method of claim 5, wherein in the first rotational state, the first gear, the second gear, and the third gear are driven by the motor.

7. The method of claim 5, further comprising:

driving, by the motor, the camshaft to a second rotational state of the plurality of rotational states;

disengaging, in the second rotational state, the first input gear from the first gear via the first power cam;

engaging, in the second rotational state, the first locker arm with the first gear via the first locker cam;

engaging, in the second rotational state, the second input gear from the second gear via the second power cam;

disengaging, in the second rotational state, the second locker arm from the second gear via the second locker cam;

disengaging, in the second rotational state, the third input gear from the third gear via the third power cam; and engaging, in the second rotational state, the third locker arm with the third gear via the third locker cam.

8. The method of claim 7, wherein in the second rotational state, the motor only drives the second gear.

9. The method of claim 7, further comprising:

driving, by the motor, the camshaft to a third rotational state of the plurality of rotational states;

disengaging, in the third rotational state, the first input gear from the first gear via the first power cam;

engaging, in the third rotational state, the first locker arm with the first gear via the first locker cam;

disengaging, in the third rotational state, the second input gear from the second gear via the second power cam;

engaging, in the third rotational state, the second locker arm with the second gear via the second locker cam;

engaging, in the third rotational state, the third input gear with the third gear via the third power cam; and disengaging, in the third rotational state, the third locker arm from the third gear via the third locker cam.

10. The method of claim 9, wherein in the third rotational state, the motor only drives the third gear.

11. A method, comprising:

driving, by a controller, a camshaft of a transmission of a telesurgically operated instrument to a first rotational state of a plurality of rotational states, wherein the camshaft defines a longitudinal axis and rotates about the longitudinal axis, and wherein the controller comprises at least one processor for controlling the transmission;

engaging, by the controller, in the first rotational state, a first input gear of a first effector drivetrain of the transmission with a first gear of the first effector drivetrain via a first power cam of the camshaft; and disengaging, by the controller, in the first rotational state, a first locker arm of the first effector drivetrain from the first gear via a first locker cam of the camshaft.

12. The method of claim 11, further comprising:

engaging, by the controller, the first effector drivetrain with a primary input gear of the transmission via the first power cam; and engaging, by the controller, the primary input gear and the first input gear with an idler gear of the transmission via the first power cam.

13. The method of claim 11, further comprising:

rotating, by the controller, in the first rotational state, the first power cam and the first locker cam 120 degrees about the longitudinal axis of the camshaft.

14. The method of claim 11, further comprising:

engaging, by the controller, in the first rotational state, a second input gear of a second effector drivetrain of the transmission with a second gear of the second effector drivetrain via a second power cam of the camshaft; and disengaging, by the controller, in the first rotational state, a second locker arm of the second effector drivetrain from the second gear via a second locker cam of the camshaft.

15. The method of claim 14, further comprising:

engaging, by the controller, in the first rotational state, a third input gear of a third effector drivetrain of the transmission with a third gear of the third effector drivetrain via a third power cam of the camshaft; and disengaging, by the controller, in the first rotational state, a third locker arm of the third effector drivetrain from the third gear via a third locker cam of the camshaft.

16. The method of claim 15, further comprising:

rotating, by the controller, the first gear, the second gear, and the third gear in sync about a longitudinal axis of a first shaft of the first effector drivetrain.

17. The method of claim 15, further comprising:

driving, by the controller, the camshaft to a second rotational state of the plurality of rotational states;

disengaging, by the controller, in the second rotational state, the first input gear from the first gear via the first power cam;

engaging, by the controller, in the second rotational state, the first locker arm with the first gear via the first locker cam;

engaging, by the controller, in the second rotational state, the second input gear with the second gear via the second power cam;

disengaging, by the controller, in the second rotational state, the second locker arm from the second gear via the second locker cam;

disengaging, by the controller, in the second rotational state, the third input gear from the third gear via the third power cam; and engaging, by the controller, in the second rotational state, the third locker arm with the third gear via the third locker cam.

18. The method of claim 17, further comprising:

rotating, by the controller, in the second rotational state, the second gear about a longitudinal axis of a second shaft of the second effector drivetrain.

19. The method of claim 17, further comprising:

driving, by the controller, the camshaft to a third rotational state of the plurality of rotational states;

disengaging, by the controller, in the third rotational state, the first input gear from the first gear via the first power cam;

engaging, by the controller, in the third rotational state, the first locker arm with the first gear via the first locker cam;

disengaging, by the controller, in the third rotational state, the second input gear from the second gear via the second power cam;

engaging, by the controller, in the third rotational state, the second locker arm with the second gear via the second locker cam;

engaging, by the controller, in the third rotational state, the third input gear with the third gear via the third power cam; and disengaging, by the controller, in the third rotational state, the third locker arm from the third gear via the third locker cam.

20. The method of claim 19, further comprising:

rotating, by the controller, in the third rotational state, the third gear about a longitudinal axis of a third shaft of the third effector drivetrain.

* * * * *